(12) United States Patent
Kawashima et al.

(10) Patent No.: US 6,451,351 B1
(45) Date of Patent: Sep. 17, 2002

(54) METHOD FOR PREPARING GEL WITH CALCIUM SALTS OF ORGANIC ACIDS

(75) Inventors: Susumu Kawashima, 19-1 Kasamai 1-chome, Kanazawa-shi, Ishikawa 920-0965 (JP); Yoshifumi Murata, Ishikawa (JP)

(73) Assignees: Meiji Milk Products Co., Ltd. (JP); Susumu Kawashima (JP)

( * ) Notice: Subject to any disclaimer, the term of this patent is extended or adjusted under 35 U.S.C. 154(b) by 0 days.

(21) Appl. No.: 09/529,603

(22) PCT Filed: Jun. 24, 1998

(86) PCT No.: PCT/JP98/02823

§ 371 (c)(1),
(2), (4) Date: Jul. 3, 2000

(87) PCT Pub. No.: WO99/20710

PCT Pub. Date: Apr. 29, 1999

(30) Foreign Application Priority Data

Oct. 16, 1997 (JP) ............................................... 9-283789

(51) Int. Cl.⁷ .......................... A61K 9/16; A23L 1/0532; B01J 13/00; C08J 3/03
(52) U.S. Cl. .......................... 424/499; 426/72; 426/573; 514/944; 514/964; 516/105; 516/106; 516/107
(58) Field of Search ................................ 516/105, 106, 516/107; 514/944, 964; 426/573; 424/499; 435/178

(56) References Cited

U.S. PATENT DOCUMENTS

| | | | | |
|---|---|---|---|---|
| 2,536,708 A | * | 1/1951 | Angermeier | 516/105 X |
| 4,400,391 A | * | 8/1983 | Connick, Jr. | 516/105 X |
| 5,071,644 A | * | 12/1991 | Viegas et al. | 514/944 X |
| 5,200,180 A | * | 4/1993 | Bannert | 514/944 X |

FOREIGN PATENT DOCUMENTS

| | | |
|---|---|---|
| JP | 52 90482 | 7/1977 |
| JP | 64 05460 | 1/1989 |
| JP | 64 25710 | 1/1989 |

OTHER PUBLICATIONS

Gatzi–Fichter, M. et al. (1941) Crystallized sodium pantothenate *Helv. Chem. Acta.* Vol. 24:185–187 (English translation is attached).

Maas, W.K., Proc. 4$^{th}$ Int. Congr. Biochem. vol. 11, p p161–168, Pergamon Press, London, 1958.

Roe, J.H. et al.(1948) *J. Biol. Chem.* 174:201–208.

* cited by examiner

*Primary Examiner*—Richard D. Lovering
(74) *Attorney, Agent, or Firm*—Saliwanchik, Lloyd & Saliwanchik

(57) ABSTRACT

A method for preparing a gel composition, such as alginate gel beads, using a proper concentration of calcium pantothenate or calcium ascorbate as a gelling agent.

14 Claims, 17 Drawing Sheets

_US 6,451,351 B1_

METHOD FOR PREPARING GEL WITH CALCIUM SALTS OF ORGANIC ACIDS

This application is a 371 of International Application No. PCT/JP98/02823, filed on Jun. 24, 1998, which, in turn, claims the benefit of Japanese Application No. 9/283,789, filed Oct. 16, 1997.

TECHNICAL FIELD

This invention relates to gelling agents and a method for preparing gels.

BACKGROUND ART

Calcium chloride or the like is usually used as a gelling agent to prepare gel compositions such as an alginate gel or others. However, when calcium chloride or the like is used as a gelling agent, it is necessary to remove the gelling agent by washing after the gel is prepared, which raises a problem of the loss of active ingredients in the gel by the washing process. Accordingly, more efficient gelling methods that do not require the washing for the removal of the gelling agent have been awaited in this technical field.

Calcium pantothenate is a member of the vitamin-B group, water-soluble vitamins. Pantothenic acid is a component of coenzyme A and participates in acyl group transfer in vivo, playing important roles in the metabolism of lipids and carbohydrates. The lack of this vitamin causes disorders of the skin, adrenal gland, peripheral nerves, digestive tracts, antibody production, reproductive function, etc. Calcium ascorbate is a member of the vitamin-C group, water-soluble vitamins. Calcium ascorbate is absorbed in the digestive tracts and widely distributed over tissues in the body in the form of ascorbic acid, which has an antiscorbutic activity, promotes platelet production, and suppresses melanogenesis. The lack of ascorbate results in the vitamin C deficiency (scurvy, etc.).

Calcium pantothenate and calcium ascorbate are currently widely used for fodders, health foods, and pharmaceuticals, etc. However, there are no reports on the applicability of these compounds as a gelling agent.

DISCLOSURE OF THE INVENTION

An objective of the present invention is to provide a more effective gelling agent and a method for preparing gel using the gelling agent. The present inventors investigated the applicability of calcium pantothenate, a member of the vitamin-B group, or calcium ascorbate, a member of the vitamin-C group, to a gelling agent, specifically, for preparing alginate gel beads. Eventually, it was found that the gel was formed-by using the calcium salts of these acids at a suitable concentration, and thus the present invention was completed.

Namely, this invention relates to a method for preparing a gel composition utilizing a calcium salt of an acid as a gelling agent, more specifically, to:

(1) a method for preparing a gel composition, the method comprising using a calcium salt of an organic acid as a gelling agent;

(2) the method as described in (1), wherein the organic acid calcium salt is calcium pantothenate or calcium ascorbate;

(3) the method as described in (1), wherein the gel composition is alginate gel composition;

(4) the method as described in (1), wherein the gel composition contains chitosan or a salt thereof;

(5) a gel composition comprising calcium pantothenate or calcium ascorbate, which is obtainable in a single-step process of gel formation by mixing an aqueous solution of a substance having gelling capability and an aqueous solution of calcium pantothenate or calcium ascorbate;

(6) the gel composition as described in (5), wherein the organic salt is selected from the group consisting of lactic acid, ascorbic acid, gluconic acid, and citric acid;

(7) the gel composition as described in (5), wherein the substance having gelling capability is sodium alginate.

A calcium salt of an organic acid for preparing gel compositions used in the present invention is not particularly limited, but preferably calcium pantothenate or calcium ascorbate.

Calcium pantothenate may be isolated from natural sources such as yeasts, the liver, and others, or may be chemically synthesized by, for example, the condensation reaction of a calcium salt of β-alanine and pantolactone to yield calcium d(+)-pantothenate (M. Catzi-Fichter: Helv. Chem. Acta., 24, 185 (1941)). In addition, pantothenic acid is known to be biosynthesized by enteric bacteria in mammals, and by yeasts, _Escherichia coli_ and _Neurospora crassa_ through the condensation of D-pantoic acid and β-alanine in the presence of ATP (W. K. Mass, Proc. 4th Int. Congr. Biochem., Vol.11, p.161, Pergamon Press, London (1960)). Pantothenic acid used in the present invention can be synthesized by any of enzymes involved in such biosynthetic reactions. It can also be produced with a bioreactor using microorganisms such as yeasts, _Escherichia coli_, and _Neurospora crassa_ mentioned above. There exist the D-enantiomer and L-enantiomer of pantothenic acid. Both calcium D-pantothenate and calcium L-pantothenate can be used as calcium pantothenate used in the present invention. Since the L-enantiomer does not possess the activity as the vitamin, the D-enantiomer should be used when the vitamin activity is required besides the function as a gelling agent.

Calcium ascorbate may be naturally occurring or chemically synthesized ones. The commercial product (Takeda Chemical Industries, Ltd.) can also be used. Ascorbic acid can be the D-enantiomer and L-enantiomer. Both calcium D-ascorbate and calcium L-ascorbate can be used as calcium ascorbate used in the present invention. The D-enantiomer does not possess the activity as the vitamin, and therefore the L-enaniomer should be used when the vitamin activity is required besides the function as a gelling agent.

A substance having gelling capability used in the method of this invention includes, for example, sodium alginate, pectin, carrageenan, agar, and gelatin. Any other substances that are gelled by calcium can be used in the method of this invention.

Chitosan used for preparing gel compositions in this invention includes chitosan having the glucosamine residue content (the degree of deacetylation) in its sugar chain of about 60% or more and average molecular weight of about 1500 to about 400,000.

When sodium alginate is used as the substance having gelling capability, a gel preparation can be produced using calcium pantothenate or calcium ascorbate by adding a 0.1 to 10% sodium alginate aqueous solution or an aqueous sodium alginate solution containing 1 to 10% chitosan dropwise to a aqueous solution of calcium pantothenate or calcium ascorbate, or a solution containing one of these calcium salts and 1 to 10% organic acid (for example, lactic acid, ascorbic acid, and gluconic acid, etc.) to form instantaneously alginate gel beads or chitosan salt-containing alginate gel beads. The concentration of calcium pantothenate used in this preparation ranges usually from about 0.03M to about 0.4M. The pH of the reaction system ranges usually from about 4.5 to about 7.0, and preferably about 6.0 to about 7.0. Calcium ascorbate is used in a concentration of about 0.02M to about 0.2M, and preferably about 0.1 to about 0.2M. The pH of the reaction system ranges usually from about 4.0 to about 7.0, and preferably about 4.5 to about 6.5. When a substance other than alginate gel is used as the substance having gelling capability, the pH in the reaction system should be adjusted so as not to inhibit the gel formation, preferably ranges from acidic to neutral pH.

Substances other than described above can be incorporated in the composition prepared by the method of this invention upon gellation. The substance to be incorporated is dissolved or suspended in a solution of alginic acid in advance, then can be easily trapped in the gel beads. The substance to be incorporated is not particularly liminted as long as it is solid or liquid. The method of this invention is advantageously applicable to substances that are decomposed by thermolysis and therefore are hardly incorporated in the gel such as agar by the conventional method. For example, multivitamin preparations can be prepared by incorporating other vitamins in the gel. When water-soluble vitamins is to be incorporated, the method of this invention is extremely advantageous in that the washing procedure to remove the gelling agent is not required. Incorporation of a chitosan salt capable of trapping taurocholic acid confers lipid metabolism-improving function on the gel preparation.

When cholestyramine, which causes constipation as the side effect, is incorporated, use of calcium pantothenate as a gelling agent can compensate the side effect of cholestyramine due to its ability to relieve constipation. Thus, the method of this inveniton is suitably applied to the manufacture of multivitamin preparations for improving lipid metabolism and vitamin-containing functional foods, which ameliorates atonic constipation. Moreover, ascorbic acid is known to reduce the cholesterol level, and accordingly, the method of this invention using calcium ascorbate as a gelling agent is suitably applied to the manufacture of pharmaceutical preparations or functional foods for treating hyperlipemia.

BEST MODE FOR CARRYING OUT THE INVENTION

The present invention will be described below in detail with reference to the following examples, but is not to be construed as being limited thereto. The materials used in Examples 1 and 2 were obtained from the following suppliers: chitosan (Kimitsu Chemical Industries Ltd., Grade F, the degree of deacetylation: 75–85%); alginic acid (NAKALAI TESQUE, INC., 500 cps); ascorbic acid (Wako Pure Chemical Industries Ltd., special grade).

EXAMPLE 1

Preparation of Alginate Gel Beads Using Calcium Pantothenate as a Gelling Agent (1) Pantothenic acid content in various alginate gel beads Alginate gel beads were formed by adding dropwise 2.0 g of a chitosan-free or 5% chitosan-containing 1% sodium alginate solution to 10 ml of 0.2M calcium pantothenate solution containing 1% lactic acid and incubating the mixture at 37° C. for 3 hours. Subsequently, pantothenic acid was separated from various alginate gel beads obtained and quantitatively measured by ion-pair chromatography using HPLC. HPLC was performed using COSMOSIL 5C-18-MS (4.6×150 mm) column and 5 mM tetrabutylammonium phosphate:methanol=3:1 as an eluate at the flow rate of 1.0 ml/minute. Detection was carried out at the wave length of 254 nm.

Figure 1:
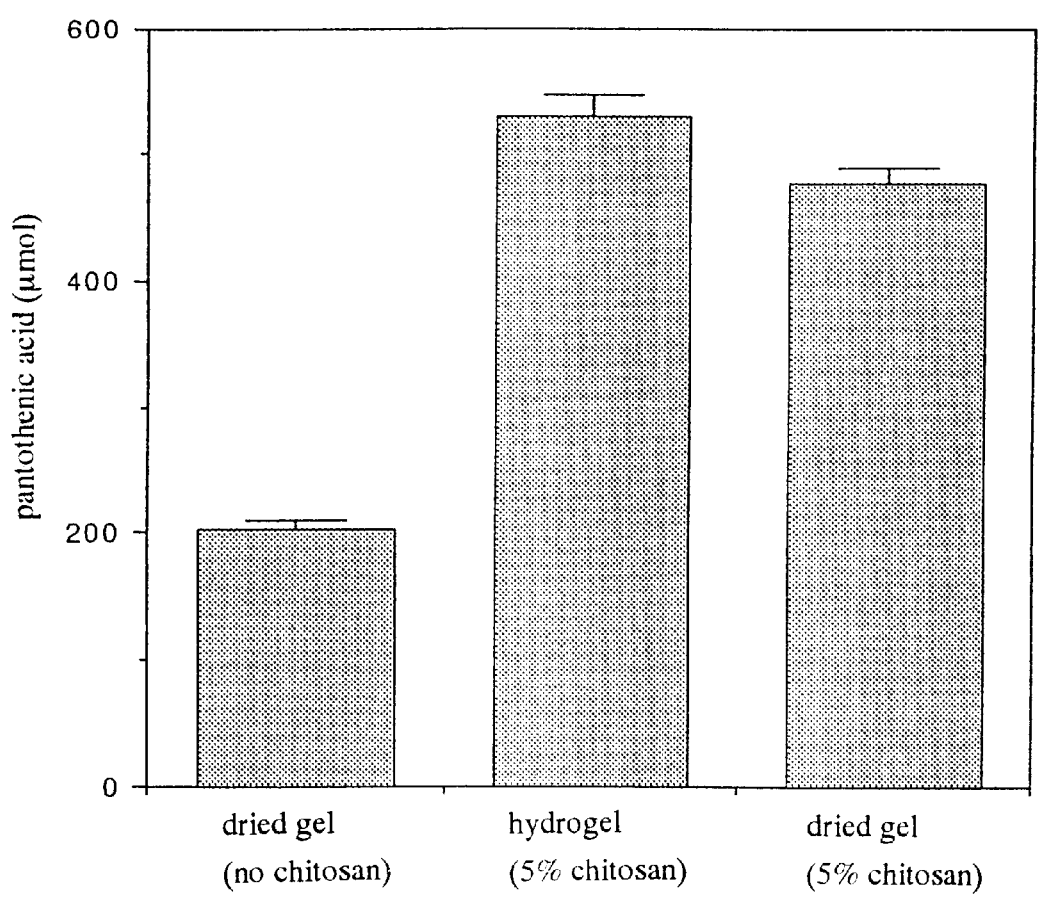
FIG. 1 is a graph showing the contents of pantothenic acid in chitosan lactate-containing or chitosan lactate-free alginate gel beads.

As shown in FIG. 1, the content of pantothenic acid was 203 μmol in the chitosan-free dry gel beads, 529 μmol in the chitosan-containing hydro-gel beads, 476 μmol in the chitosan-containing dry gel beads. Thus, the content of pantothenic acid was higher in the chitosan salt-containing alginate gel beads than in the chitosan salt-free alginate gel beads.

Figure 2:
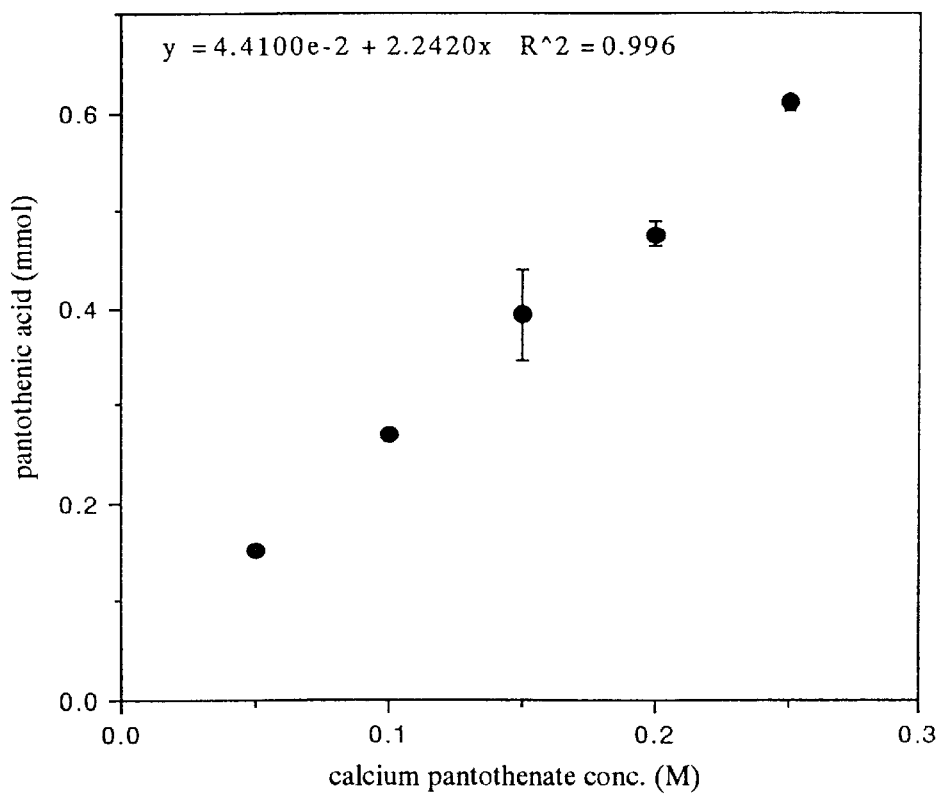
FIG. 2 is a graph showing the contents of pantothenic acid plotted against the concentration of calcium pantothenate used as a gelling agent.

(2) Relationship between the pantothenic acid content in alginate gel beads and the calcium pantothenate concentration used for gel preparation Chitosan salt-embedded alginate gel beads were formed by the same method described in (1). The relationship between the calcium pantothenate concentration and the pantothenic acid content in the alginate gel beads was investigated, varying the calcium pantothenate concentration to 0.05M, 0.1M, 0.15M, 0.2M, and 0.25M. The pantothenic acid content in the alginate gel beads was measured by the same method as described in (1). As can be seen in FIG. 2, the pantothenic acid content in the alginate gel beads was increased depending on the calcium pantothenate concentration used for gel preparation.

(3) Releasing behavior of pantothenic acid from the alginate gel beads

The content of pantothenic acid released from the alginate gel beads prepared by the same method as described in (1) was measured with the passage of time. The measurement was carried out by HPLC or ONPH. HPLC was performed using COSMOSIL 5C-18-MS (4.6×150 mm) column and 5 mM tetrabutylammonium phosphate:methanol=3:1 as an eluate at the flow rate of 1.0 ml/minute. Detection was performed with a UV detector. The ONPH method was performed by adding 1 ml of a 0.41N hydrochloric acid solution containing 10 mM ONPH·HCl to 2 ml of a sample, further adding 1 ml of a 4% (v/v) pyridine solution containing 0.15M carbodiimide (EDC) thereto, and incubating the mixture at 40° C. for 30 minutes. Then, 1 ml of 1.5N NaOH was added to the reaction mixture, which was incubated at 60° C. for 15 minutes, followed by detection using a spectrometer.

Figure 3:
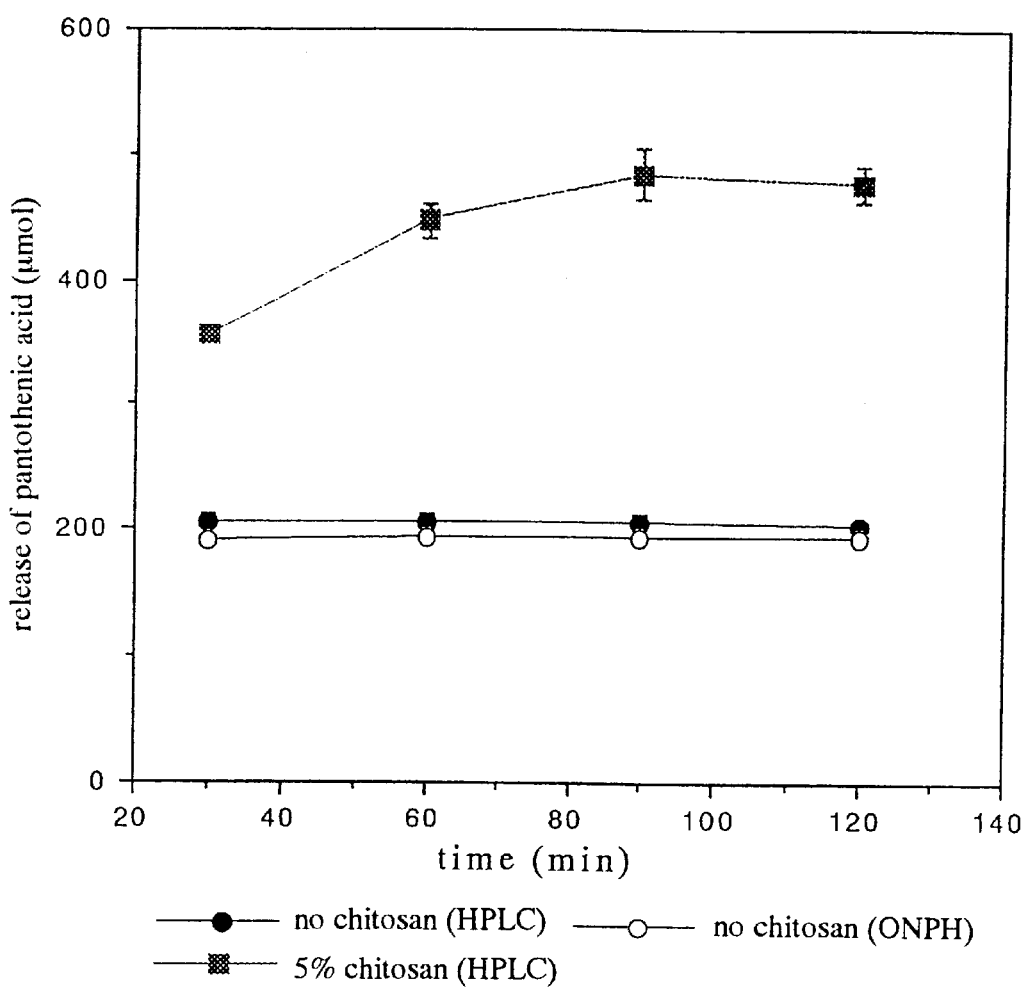
FIG. 3 is a graph showing the time-dependent pantothenic acid-releasing behavior of chitosan lactate-containing or chitosan lactate-free alginate gel beads.

The results are shown in FIG. 3. When measured by HPLC, more pantothenic acid was released from the chitosan-containing gel beads than from the chitosan-free gel beads. The amount of pantothenic acid released from the chitosan-free gel beads measured by ONPH almost agreed with that measured by HPLC.

Figure 4:
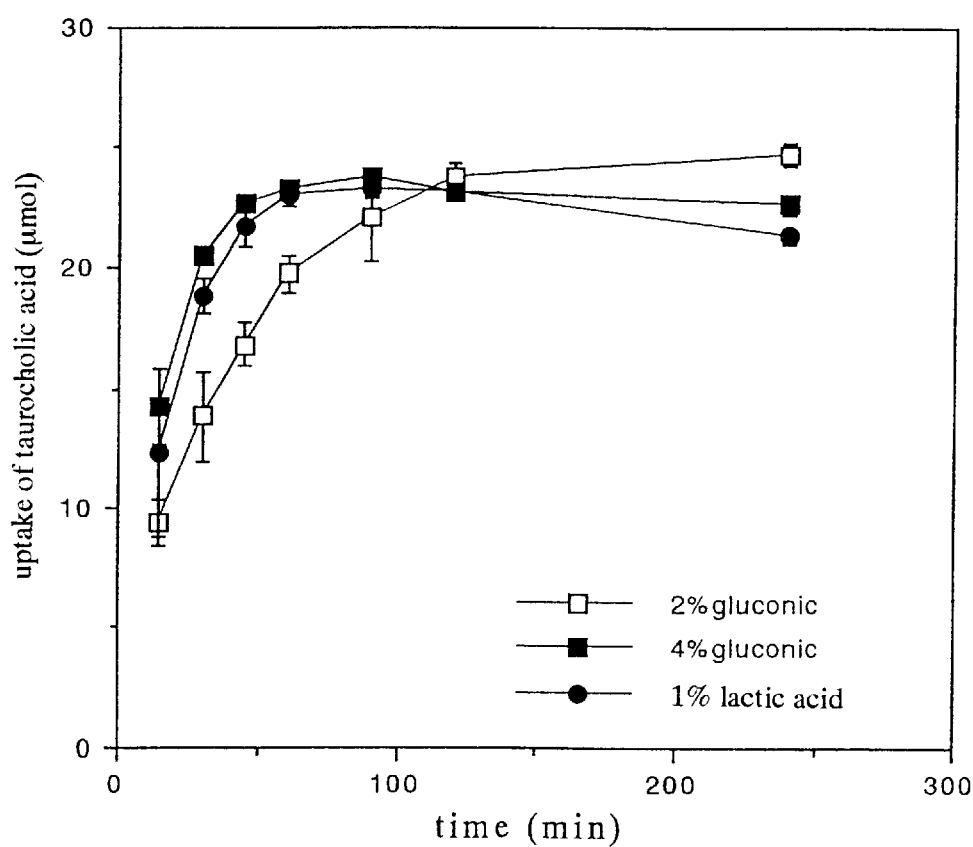
FIG. 4 is a graph showing the uptake of taurocholic acid by chitosan lactate-containing or chitosan gluconate-containing alginate gel beads.

(4) Uptake of taurocholic acid by various chitosan salt-embedded alginate gel beads The chitosan salt-embedded alginate gel beads were formed by the same method as described in (1), except for using 2% gluconic acid, 4% gluconic acid, or 1% lactic acid as a weak acid. The dry gel beads (about 50 mg in dry weight) prepared by the method described in (1) were added to 15 ml of 2 mM taurocholic acid solution in a L-shaped tube. While the tube was shaken at 67 rpm at 37° C., aliquots of the aqueous sample were taken with the passage of time, and the amount of taurocholic acid in the system was measured by HPLC. HPLC was performed using COSMOSIL 5C-18-MS (4.6×150 mm) column and methanol:30 mM phosphate buffer (pH 3.4):acetonitrile=6:3:1 as an eluate at the flow rate of 0.8 ml/minute. Detection was carried out at the wave length of 235 nm. The result is shown in FIG. 4. As shown in FIG. 4, sufficient uptake of taurocholic acid was observed in the gel beads prepared using gluconic acid or lactic acid as a weak acid. Uptake of taurocholic acid was less by the gel beads prepared using 2% gluconic acid than by those prepared using 4% gluconic acid up to about 70 minutes from the initiation of the measurement, whereas the oppposite result was obtained after 100 minutes from the initiation of the measurement.

Figure 5:
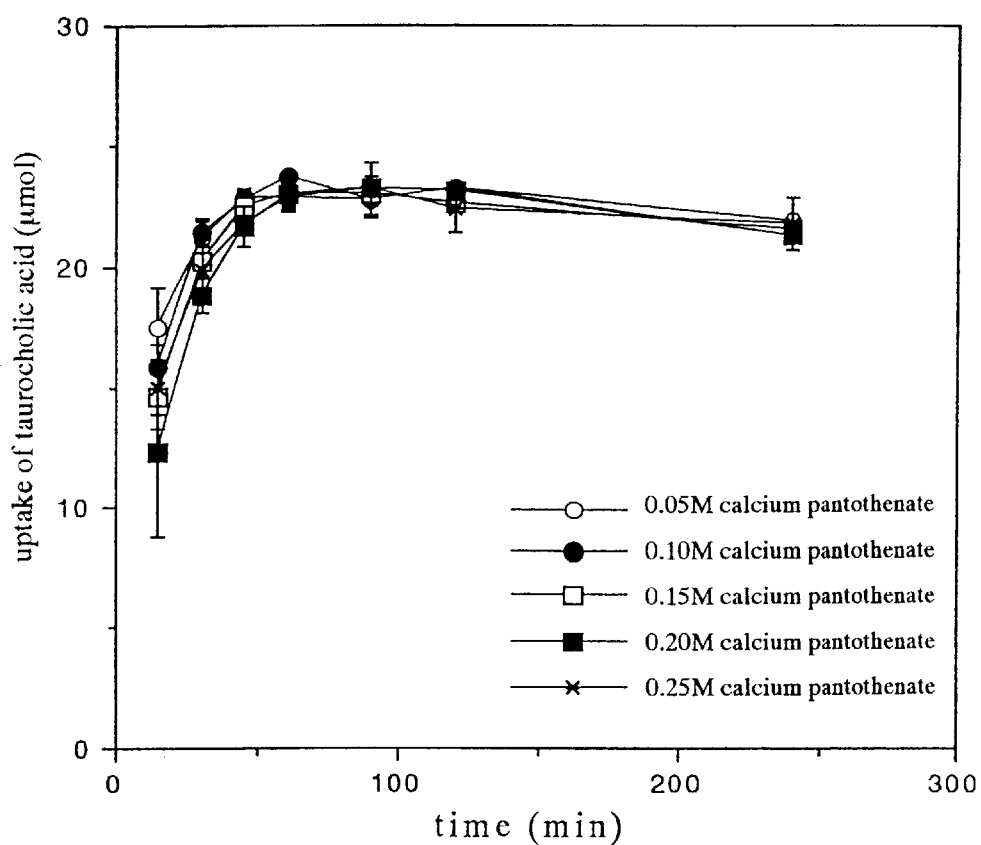
FIG. 5 is a graph showing the influence of the calcium pantothenate concentration at the time of gellation on the uptake of taurocholic acid by chitosan lactate-containing alginate gel beads.

(5) Effect of the calcium pantothenate concentration at the time of gel preparation on uptake of taurocholic acid by the chitosan salt-containing alginate gel beads The chitosan salt-containing alginate gel beads were formed by the same method as described in (1), except for varying the calcium pantothenate concentration to 0.05M, 0.1M, 0.15M, 0.2M, and 0.25M. The effect of the calcium pantothenate concentration at the time of gel preparation on the taurocholic acid uptake by the chitosan salt-containing alginate gel beads was investigated by measuring in the course of time the taurocholic acid uptake by the chitosan-containing alginate gel beads in the same manner as in (4). No influence of the calcium pantothenate concentration at the time of gel preparation on the taurocholic acid uptake by the chitosan salt-containing alginate gel beads was observed as shown in FIG. 5.

Figure 6:
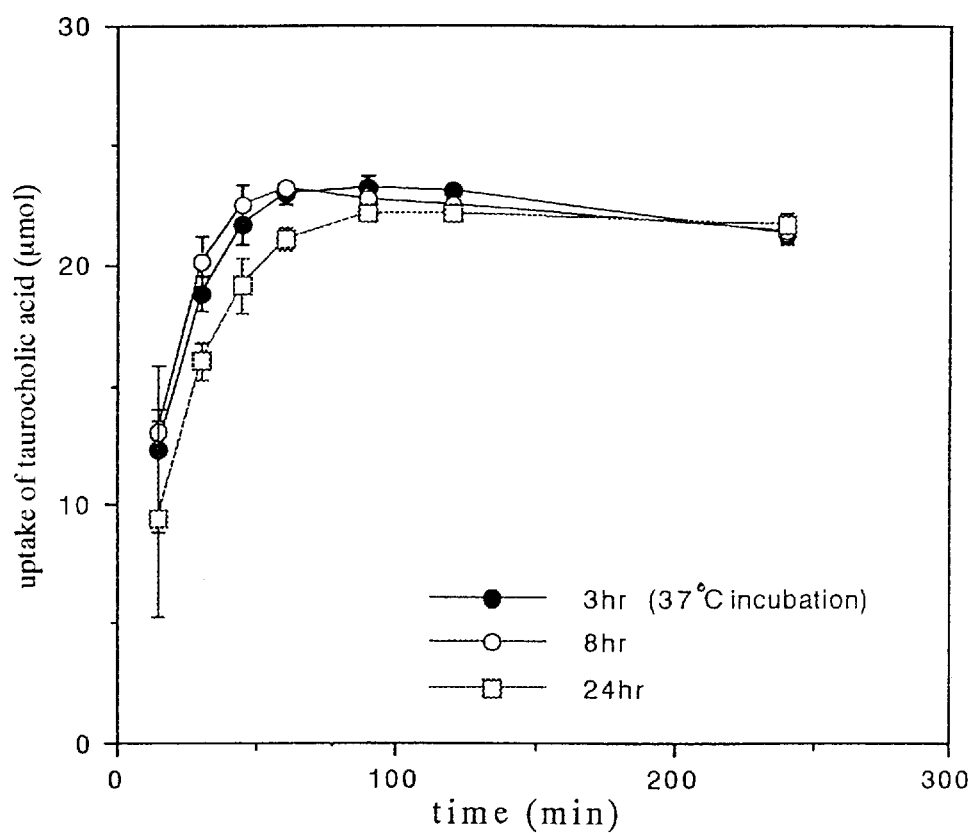
FIG. 6 is a graph showing the influence of the incubation time for preparing chitosan lactate-containing alginate gel beads on the uptake of taurocholic acid by the gel beads.

(6) Effect of the time required for preparing the alginate gel beads on the taurocholic acid uptake by the chitosan salt-immobilized gel beads The chitosan salt-embedded alginate gel beads were prepared by the same method as described in (1) except for varying the incubation time to 3 hours, 8 hours, and 24 hours. The effect of the gel preparation time on the taurocholic acid uptake by the gel beads was investigated by measuring in the course of time the taurocholic acid uptake in the same manner as in (4). As shown in FIG. 6, almost no influence of the time required for the gel preparation on the taurocholic acid uptake by the chitosan salt-immobilized alginate gel beads was observed.

EXAMPLE 2

Preparation of Alginate Gel Beads Using Ascorbate Calcium as a Gelling Agent (1) Method for preparing alginate gel beads containing ascorbic acid and chitosan(method A) and the taurocholic acid uptake by the gel beads The alginate gel beads were formed by adding 2.0 g of 1% sodium alginate solution containing 5% chitosan to 10 ml of 0.1M or 0.2M calcium ascorbate solution and incubating the mixture at room temperature for 2 hours. The thus-obtained alginate gel beads were added to 500 ml of a weak acid solution. The mixture was allowed to stand at room temperature for 24 hours to embed the chitosan salt in the gel. The hydro-gel beads were thus obtained. The hydrogel beads were dried to prepare the dry gel beads (method A).

Figure 7:
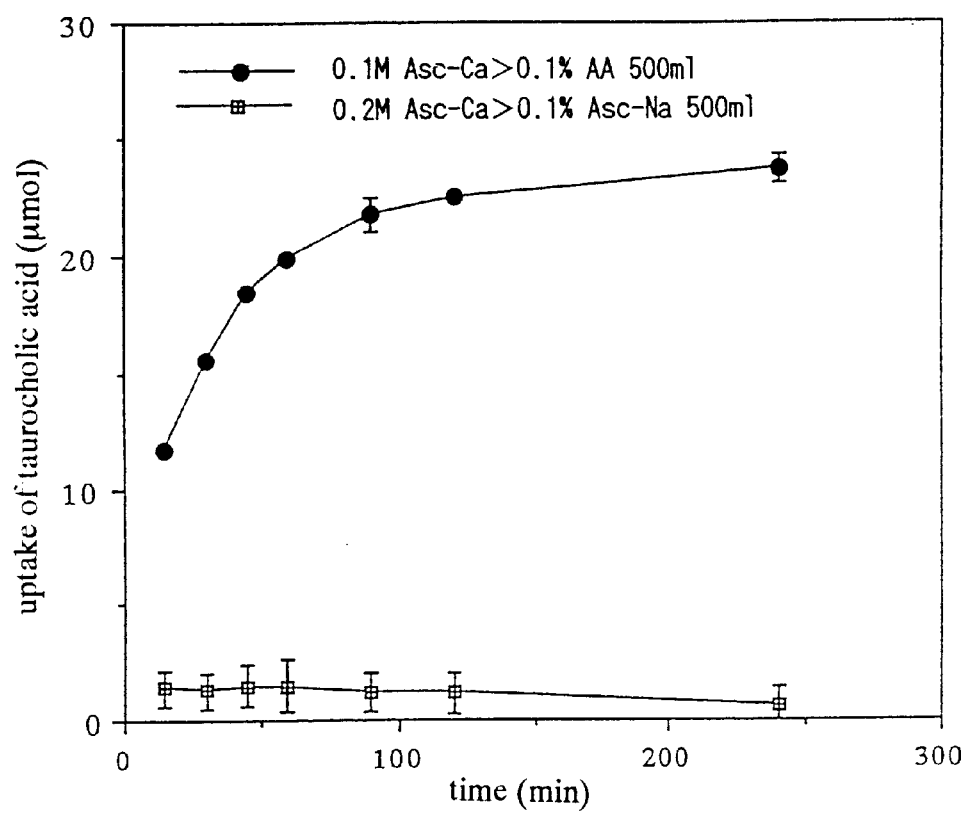
FIG. 7 shows the difference in the uptake of taurocholic acid by the gel beads prepared by method A (Example 2(1)) using 0.1% ascorbic acid (AA) or calcium ascorbate (Asc-Ca) as a weak acid.
Figure 8:
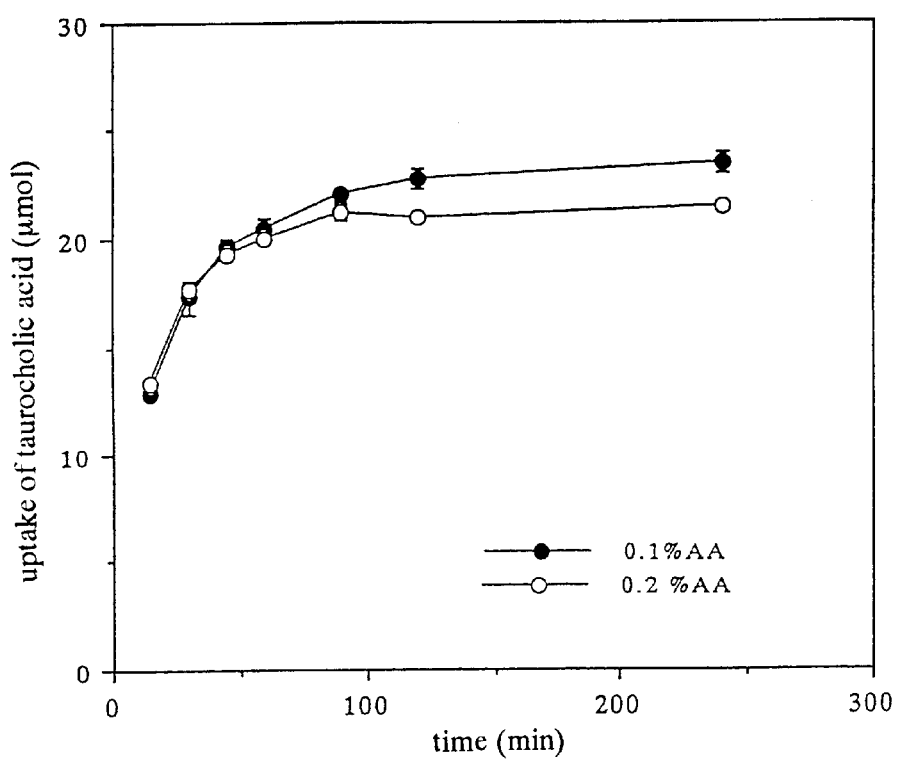
FIG. 8 shows the uptake of taurocholic acid by the gel beads prepared by method A using 0.1 or 0.2% ascorbic acid (AA) as a weak acid.

The hydro-gel beads were prepared by method A using 0.1% ascorbic acid as a weak acid or using 0.1% sodium ascorbate, and the taurocholic acid uptake by the hydro-gel beads was examined. The hydro-gel beads (2 g) were added to the L-shaped tube containing 15 ml of a 2 mM taurocholic acid aqueous solution. While the tube was shaken at 67 rpm at 37° C., the mixture was sampled from the tube with the passage of time, and the taurocholic acid in the system was measured by HPLC to determine the taurocholic acid uptake. HPLC was performed using COSMOSIL 5C-18-MS (4.6×150 mm) column and methanol:30 mM phosphate buffer:acetonitrile=6:3:1 as an eluate at the flow rate of 0.8 ml/minute. Detection was carried out at the wave length of 235 nm. The result showed that sufficient taurocholic acid uptake was detected when ascorbic acid was used as a weak acid, while no significant uptake of taurocholic acid was detected by the gel beads prepared using sodium ascorbate (FIG. 7). The same experiment was performed using the hydro-gel beads prepared by using 0.1% ascorbic acid and 0.2% ascorbic acid as a weak acid. No significant difference was detected in the taurocholic acid uptake by the two gels (FIG. 8).

Figure 9:
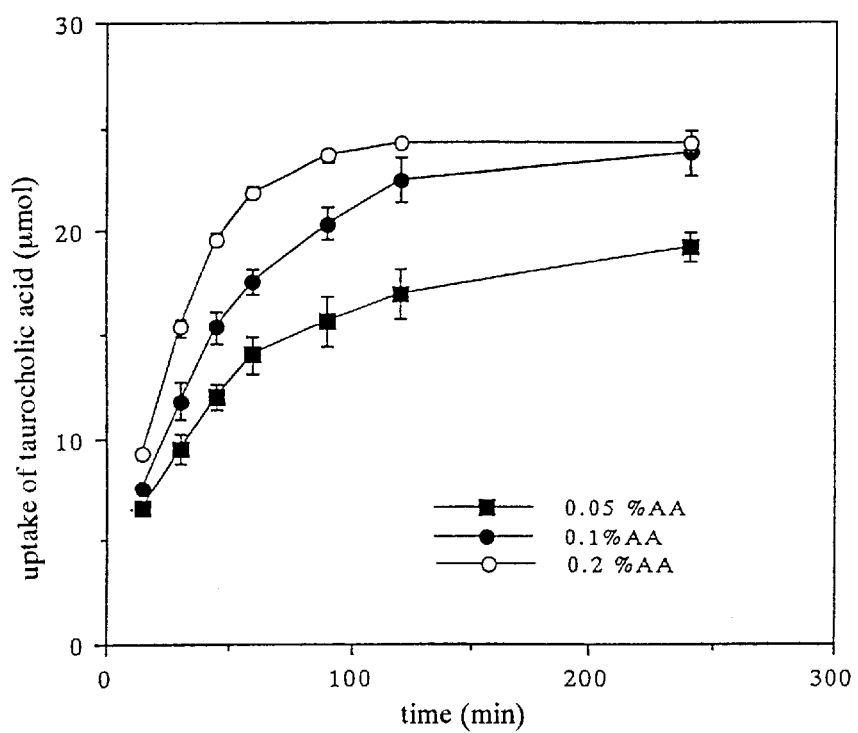
FIG. 9 shows the uptake of taurocholic acid by the dry gel beads prepared by method A using 0.05, 0.1, or 0.2% ascorbic acid (AA) as a weak acid.

In addition, the dry gel beads were prepared by method A using 0.05, 0.1, and 0.2% ascorbic acid as a weak acid. The taurocholic acid uptake by the resulting dry gel beads was measured by the same method as described above. As a result, no significant difference was detected in the taurocholic acid uptake by the gel beads prepared using ascorbic acid with a concentration of 0.1% or higher (FIG. 9).

Figure 10:
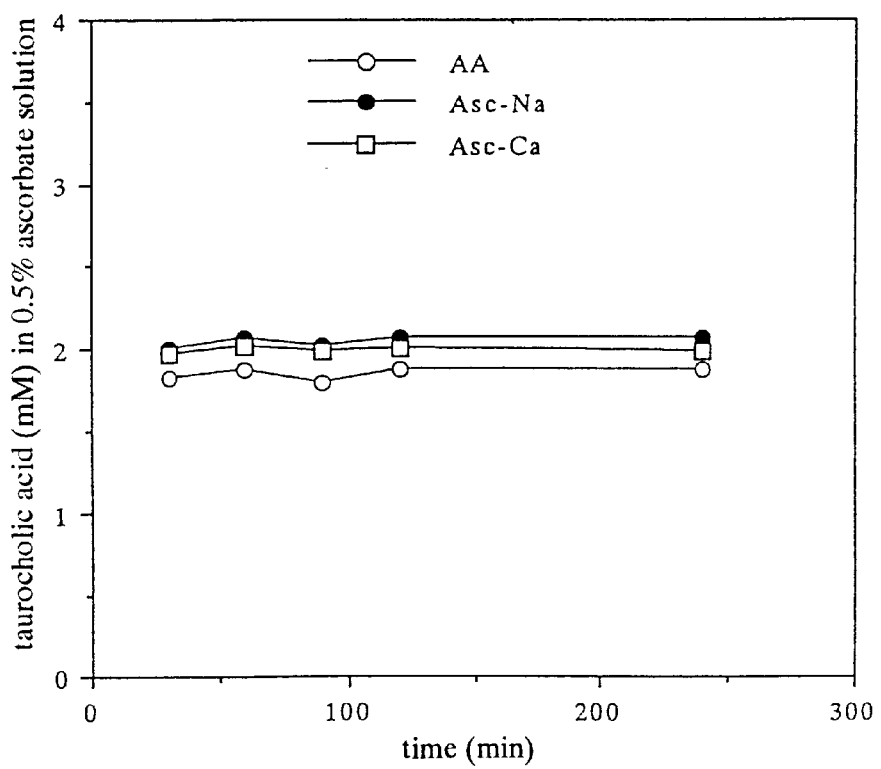
FIG. 10 shows the time-course of the influence of ascorbic acid (AA), sodium ascorbate (Asc-Na), or calcium ascorbate (Asc-Ca) added to a taurocholic acid solution on the uptake of taurocholic acid by the respective gel beads prepared by method A.

To analyze the influence of solvents on the taurocholic acid uptake, 5% ascorbic acid or 0.15 ml of salts thereof was added to 15 ml of a taurocholic acid solution in a L-shaped tube, and the mixture was shaken at 37° C. The time-course change of the amount of taurocholic acid was monitored. No change of the taurocholic acid amount was detected (FIG. 10).

(2) Method for preparing the alginate gel beads containing both ascorbic acid and chitosan (method B) and the taurocholic acid uptake by the gel beads The hydro-gel beads were prepared by adding 2.0 g of a 1% sodium alginate solution containing 5% chitosan to 10 ml of a calcium ascorbate solution containing a weak acid and incubating the mixture at 37° C. for 2 hours to embed chitosan salt in the gel. The hydro-gel beads were dried to prepare the dry gel beads (method B). This method does not require to wash the gel with a large volume of a weak acid, and is thus industrially advantageous.

Figure 11:
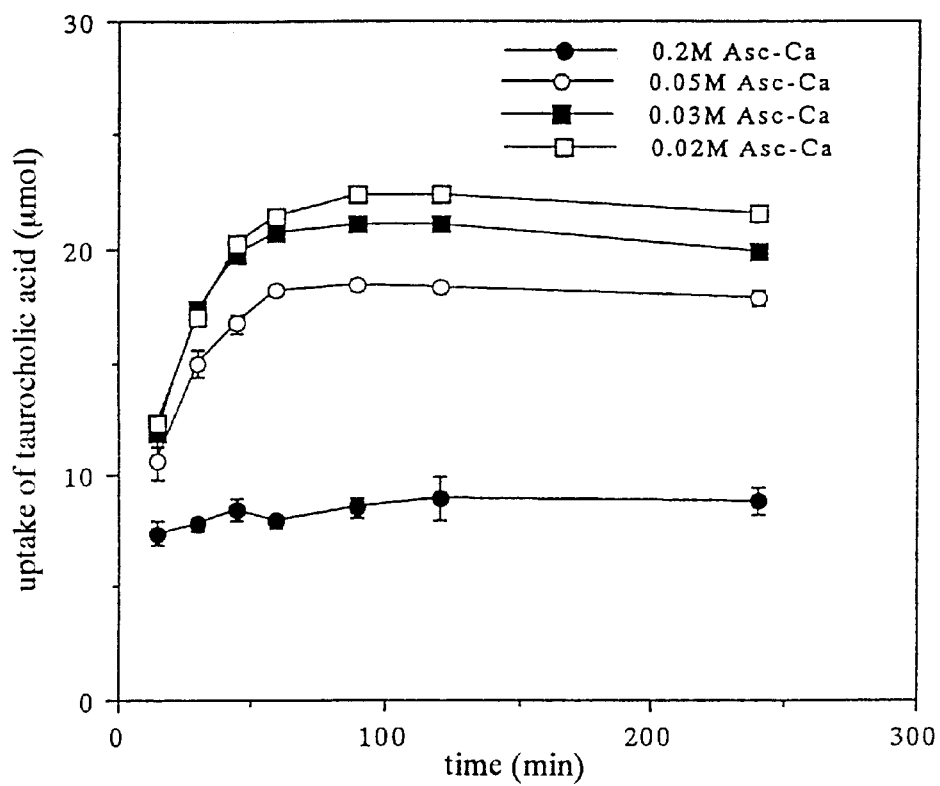
FIG. 11 shows the uptake of taurocholic acid by the gel beads prepared by method B (Example 2(2)) using 0.02 to 2 M calcium ascorbate (Asc-Ca) as a gelling agent and 1% ascorbic acid (AA) as a weak acid.

Gel beads were prepared using 0.02 to 0.2 M calcium ascorbate as a gelling agent and 1% ascorbic acid as a weak acid, and the taurocholic acid uptake by the gel beads was measured by the same method as described in Example 2 (1). As a result, sufficient taurocholic acid uptake was observed when calcium ascorbate was used in a concentration of 0.02 M, 0.03 M, or 0.05 M (FIG. 11).

Figure 12:
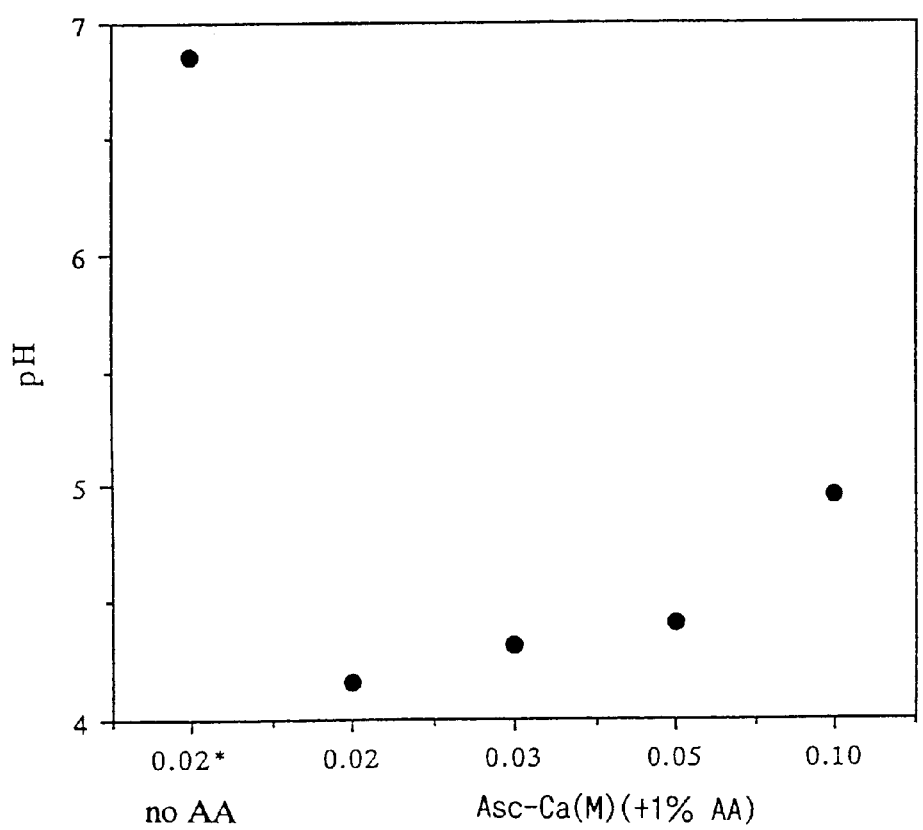
FIG. 12 shows the relationship between the pH and the amount of calcium ascorbate in method B using 1% ascorbic acid (AA) as a weak acid.

Subsequently, the relationship between the amount of calcium ascorbate added as a gelling agent and the pH of the system when 1% ascorbic acid was used as a weak acid was assessed. The result is shown in FIG. 12. Chitosan ascorbate was formed in the ascorbic acid-calcium ascorbate buffer (about pH 4 to 5). Thus, lower pHs in the system are advantageous in the chitosan-salt formation, and more taurocholic acid molecules can be taken by the resulting gel (FIG. 11).

Figure 13:
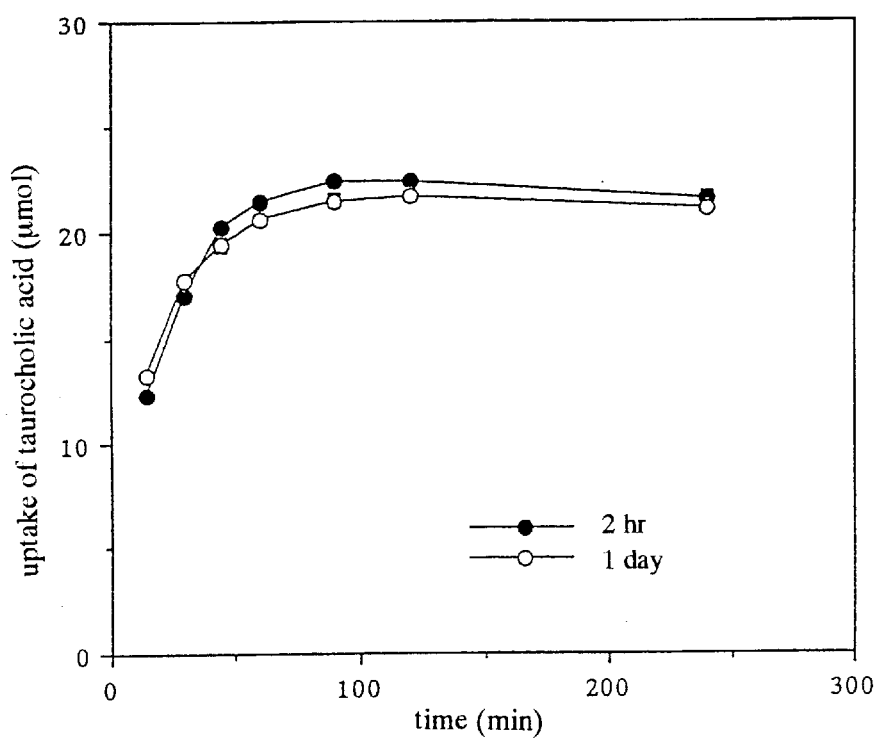
FIG. 13 shows the uptake of taurocholic acid by the gel beads prepared by method B using 0.02 M calcium ascorbate (Asc-Ca) as a gelling agent and 1% ascorbic acid (AA) as a weak acid. The treatment with ascorbic acid (AA) was continued for 2 hours or 1 day.

Next, the hydro-gel beads were prepared by method B using 0.02 M calcium ascorbate as a gelling agent and 1% ascorbic acid as a weak acid and incubating the system with the ascorbic acid for 2 hours or 1 day. The relationship between the period of the ascorbic acid treatment and the taurocholic acid uptake was assessed. No significant difference was obserbed between the 2-hour and 1-day treatments (FIG. 13).

(3) Method for preparing the alginate gel beads containing ascorbic acid and chitosan (method-C) and the taurocholic acid uptake by the gel beads The alginate gel beads were prepared by adding 2.0 g of a 1% sodium alginate solution containing 5% chitosan to 10 ml of a calcium ascorbate solution and incubating the mixture at 37° C. for 2 hours. The obtained alginate gel beads were then added to 90 ml of a weak acid solution, the mixture was allowed to stand at room temperature for 24 hours, and the chitosan salt was allowed to be embedded in the gel to prepare the hydro-gel beads. The hydro-gel beads were dried to prepare the dry gel beads (method C).

Figure 14:
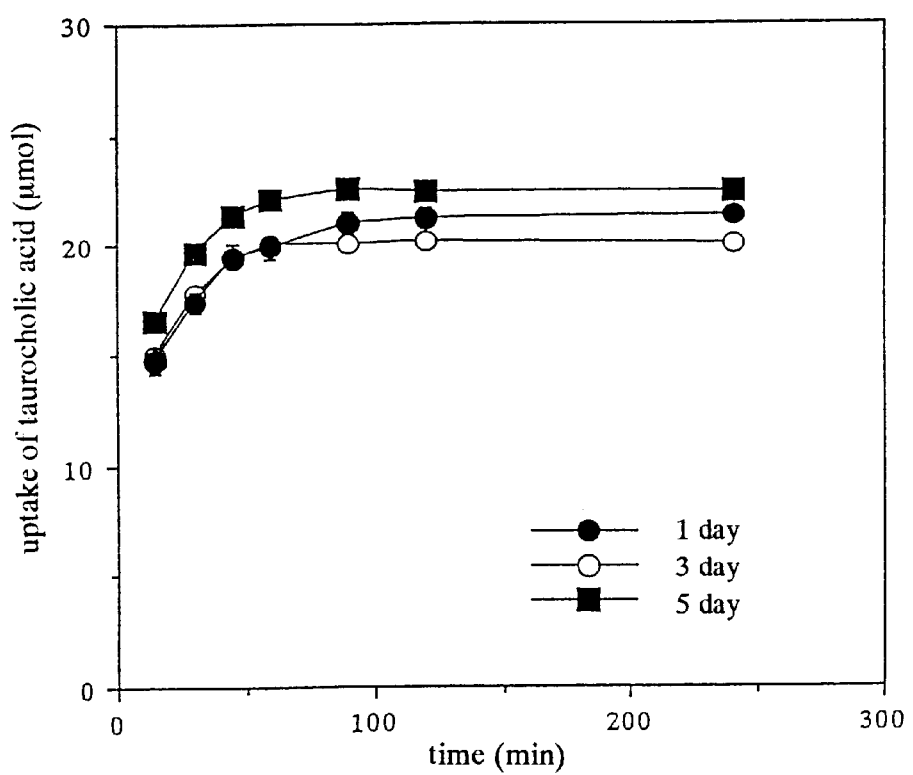
FIG. 14 shows the uptake of taurocholic acid by the gel beads prepared by method C (Example 2(3)) using 0.02 M calcium ascorbate (Asc-Ca) as a gelling agent and 0.2% ascorbic acid (AA) as a weak acid. The treatment with the weak acid was continued for 1, 3 or 5 days.

The hydro-gel beads were prepared using 0.02 M calcium ascorbate as a gelling agent and 0.2% ascorbic acid as a weak acid and incubating the system with the weak acid for 1 day, 3 days or 5 days, and the taurocholic acid uptake was examined. In any treating time, sufficient taurocholic acid uptake was observed (FIG. 14).

Figure 15:
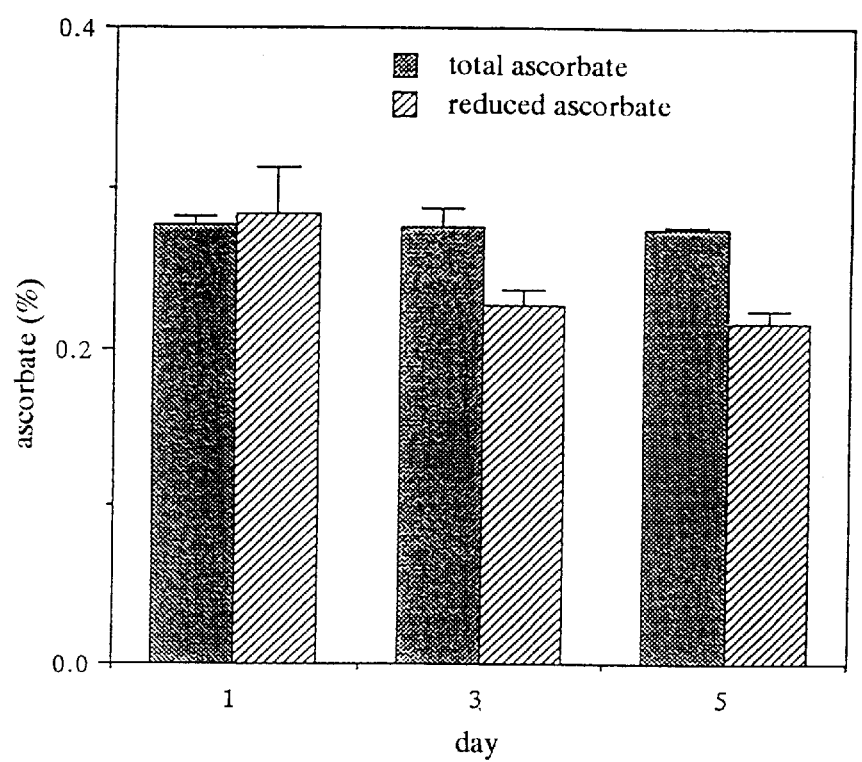
FIG. 15 shows the structural change of ascorbic acid in hydro-gel beads prepared by method C.

The structural change of ascorbic acid in the prepared hydro-gel beads was also assessed to confirm that the activity of ascorbic acid as vitamin C was not decreased due to its decomposition or degeneration when preserved in an aqueous solution containing the alginate gel beads. The total amount of ascorbic acid was determined by the Dinitrophenylhydrazine method (J. H. Roe, et al., J. Biol. Chem. 174, 201 (1948)). Reduced ascorbic acid was detected using F kit (Boerhinger-Mannheim). As a result, there observed no significant difference in the total amount of ascorbic acid due to the varied weak-acid treatment time, while the amount of reduced ascorbic acid was decreased in the samples treated with the weak acid for 3 days or 5 days (FIG. 15).

Figure 16:
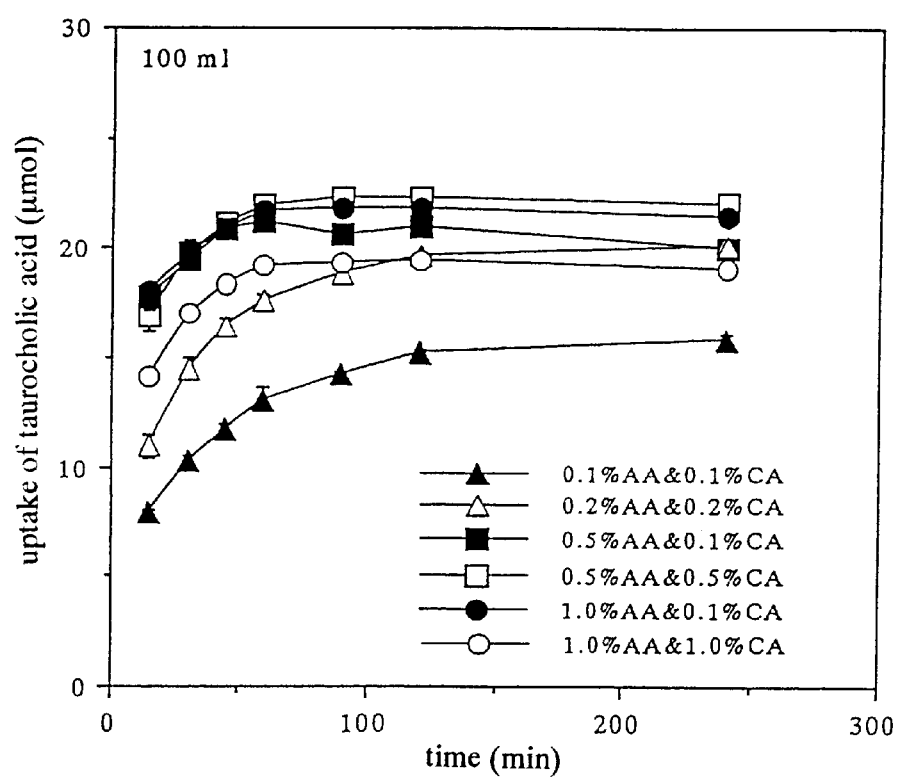
FIG. 16 shows the uptake of taurocholic acid by the gel beads prepared by method C using 0.02 M calcium ascorbate (Asc-Ca) as a gelling agent and, as weak acids, ascorbic acid (AA) and citric acid (CA) in various combinations of their concentrations.

Next, the hydro-gel beads were prepared using 0.02 M calcium ascorbate as a gelling agent and using as a weak acid a mixture of ascorbic acid and citric acid that is used as an additive for drinks, varying the mixing ratio. The gels were treated with the weak acid mixture for 1 day, and the taurocholic acid uptake was assayed. The result revealed that the most excellent taurocholic acid uptake was observed with the gel beads that were treated with a combination of 0.5% ascorbic acid and 0.5% citric acid or in a combination of 1.0% ascorbic acid and 0.1% citric acid (FIG. 16).

Figure 17:
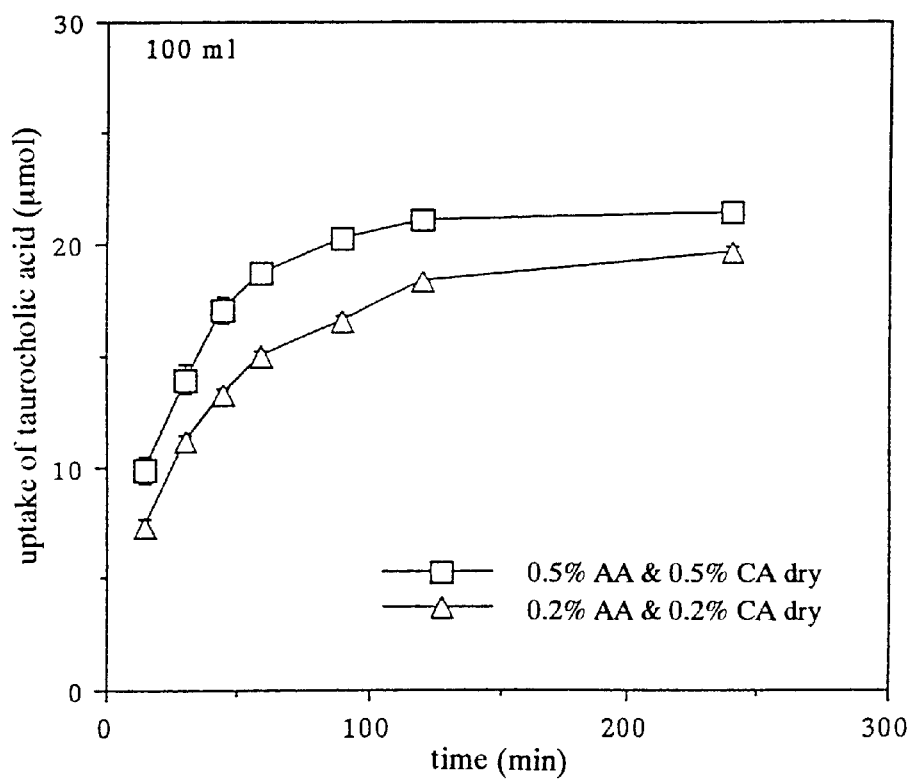
FIG. 17 shows the uptake of taurocholic acid by the gel beads prepared by method C using 0.02 M calcium ascorbate (Asc-Ca) as a gelling agent and ascorbic acid (AA) and citric acid (CA) as weak acids.

Separately, the dry gel beads were prepared by method C using 0.02 M calcium ascorbate as a gelling agent, in which the gels were treated with a mixture of ascorbic acid and citric acid as a weak acid for 1 day. The taurocholic acid uptake was assayed. As a result, sufficient taurocholic acid uptake was observed by the dry gel beads treated with a combination of 0.5% ascorbic acid and 0.5% citric acid or a combination of 0.2% ascorbic acid and 0.2% citric acid (FIG. 17).

Industrial Applicability

The present invention provides a method for preparing gel using a calcium salt of an acid as a gelling agent. The method of this invention does not require washing for removing a gelling agent after the preparation of gel, and thus is an extremely efficient method.

When calcium pantothenate or calcium ascorbate is used as a gelling agent, the gel prepared using it can be a useful vitamin preparation because these calcium salts originally function as vitamins and they are released from the gel after taken.

Furthermore, calcium pantothenate or calcium ascorbate might play useful roles by cooperating with a substance embedded in the gel. For example, when cholestyramine, an anti-hyperlipemia drug, is embedded in the gel, calcium pantothenate that enhances the intestinal motility can reduce constipation caused by cholestyramine as the side effect. Ascorbic acid is known to lower the blood-cholesterol level, and, when cholestyramine is embedded in the gel prepared using ascorbate as a gelling agent, the prepared gel can be suitable as a pharmaceutical preparation or functional food for treating hyperlipemia.

The method of this invention also enables embedding other substances in the gel. For example, multivitamin preparations can be prepared by embedding other vitamins. Furthermore, since the chitosan salt-embedded gel takes up taurocholic acid, it can be used as a pharmaceutical preparation for improving lipid metabolism.

What is claimed is:

1. A method for preparing a gel composition for oral administration, the method comprising mixing a first aqueous solution comprising a substance having a gelling capability, with a second aqueous solution comprising a gelling agent selected from the group consisting of (a) calcium pantothenate and an organic acid, and (b) calcium ascorbate.

2. The method of claim 1, wherein the second aqueous solution further comprises an organic acid when the gelling agent is calcium ascorbate.

3. The method of claim 1, wherein the gel composition is alginate gel composition.

4. The method of claim 3, wherein the gel composition further contains chitosan or a salt thereof.

5. The method according to claim 1, wherein the organic acid is selected from the group consisting of lactic acid, ascorbic acid, gluconic acid, and citric acid.

6. A gel composition for oral administration comprising calcium pantothenate or calcium ascorbate, which is obtainable in a single-step process of gel formation by mixing an aqueous solution of a substance having gelling capability with and an aqueous solution comprising (i) calcium pantothenate or calcium ascorbate and (ii) an organic acid.

7. The gel composition of claim 6, wherein the organic salt is selected from the group consisting of lactic acid, ascorbic acid, gluconic acid, and citric acid.

8. The gel composition of claim 6, wherein the substance having gelling capability is sodium alginate.

9. The gel composition of claim 6, wherein said gel composition comprises a vitamin, food supplement, or pharmaceutical preparation.

10. The gel composition of claim 6, wherein said gel composition further includes a pharmaceutically active agent embedded therein.

11. The gel composition of claim 10, wherein said pharmaceutically active agent is cholestyramine.

12. The gel composition of claim 11, wherein said substance having gelling capability is calcium pantothenate, further wherein said gel composition reduces constipation caused by cholestyramine by enhancing intestinal motility.

13. The gel composition of claim 11, wherein said substance having gelling capability is calcium ascorbate, further wherein said gel composition reduces blood cholesterol levels.

14. The gel composition of claim 6, wherein said gel composition further contains chitosan or a salt thereof, wherein said gel composition improves lipid metabolism.

* * * * *